US00PP28651P3

(12) United States Plant Patent
Holtmaat

(10) Patent No.: US PP28,651 P3
(45) Date of Patent: Nov. 14, 2017

(54) ***ECHINACEA* PLANT NAMED 'MINBEL252'**

(50) Latin Name: *Echinacea hybrida*
Varietal Denomination: Minbel252

(71) Applicant: Henricus Maria Joseph Holtmaat, Zuidwolde (NL)

(72) Inventor: Henricus Maria Joseph Holtmaat, Zuidwolde (NL)

(73) Assignee: AB Kwekersrechten B.V., Zuidwolde (NL)

( * ) Notice: Subject to any disclaimer, the term of this patent is extended or adjusted under 35 U.S.C. 154(b) by 69 days.

(21) Appl. No.: 14/756,669

(22) Filed: Sep. 29, 2015

(65) Prior Publication Data

US 2017/0094887 P1 Mar. 30, 2017

(51) Int. Cl.
*A01H 5/02* (2006.01)

(52) U.S. Cl.
USPC ..... Plt./428

(58) Field of Classification Search
USPC ..... Plt./428
See application file for complete search history.

(56) References Cited

PUBLICATIONS

AB Cultivars Breeding for Better Gardens retrieved on Jan. 19, 2015, retrieved from the Internet at <http://www.ab-cultivars.com/en/assortment/echinacea-mini-belle/> one page.*

* cited by examiner

*Primary Examiner* — June Hwu
(74) *Attorney, Agent, or Firm* — C. A. Whealy

(57) ABSTRACT

A new and distinct cultivar of *Echinacea* plant named 'Minbel252', characterized by its upright and relatively compact plant habit; vigorous growth habit; freely branching habit; strong flowering stems; numerous large anemone-centered inflorescences with red purple-colored florets; and good garden performance.

2 Drawing Sheets

Botanical designation: *Echinacea hybrida.*
Cultivar denomination: 'MINBEL252'.

BACKGROUND OF THE INVENTION

The present invention relates to a new and distinct cultivar of *Echinacea* plant, botanically known as *Echinacea hybrida*, and hereinafter referred to by the name 'Minbel252'.

The new *Echinacea* plant is a product of a planned breeding program conducted by the Inventor in Zuidwolde, The Netherlands. The objective of the breeding program is to develop new freely flowering and relatively compact *Echinacea* plants with unique and attractive ray floret coloration.

The new *Echinacea* plant originated from a cross-pollination in July, 2011 in Zuidwolde, The Netherlands of *Echinacea hybrida* 'Southern Belle', disclosed in U.S. Plant Pat. No. 23,493, as the female, or seed, parent with a proprietary selection of *Echinacea hybrida* identified code number 808-25, not patented, as the male, or pollen, parent. The new *Echinacea* plant was discovered and selected by the Inventor as a single flowering plant from within the progeny of the stated cross-pollination grown in a controlled greenhouse environment in Zuidwolde, The Netherlands in June, 2012.

Asexual reproduction of the new *Echinacea* plant by in vitro meristem culture in a controlled environment in Zuidwolde, The Netherlands since July, 2014 has shown that the unique features of this new *Echinacea* plant are stable and reproduced true to type in successive generations.

SUMMARY OF THE INVENTION

Plants of the new *Echinacea* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Minbel252'. These characteristics in combination distinguish 'Minbel252' as a new and distinct *Echinacea* plant:

1. Upright and relatively compact plant habit.
2. Vigorous growth habit.
3. Freely branching habit.
4. Strong flowering stems.
5. Numerous large anemone-centered inflorescences with red purple-colored florets.
6. Good garden performance.

Plants of the new *Echinacea* can be compared to plants of the female parent, 'Southern Belle'. Plants of the new *Echinacea* differ from plants of 'Southern Belle' in the following characteristics:

1. Plants of the new *Echinacea* are shorter than plants of 'Southern Belle'.
2. Plants of the new *Echinacea* have stronger flowering stems than plants of 'Southern Belle'.
3. Ray florets of plants of the new *Echinacea* are lighter red purple in color than ray florets of plants of 'Southern Belle'.

Plants of the new *Echinacea* can be compared to plants of the male parent selection. Plants of the new *Echinacea* differ from plants of the male parent selection in the following characteristics:

1. Plants of the new *Echinacea* are shorter than plants of the male parent selection.
2. Ray florets of plants of the new *Echinacea* are darker red purple in color than ray florets of plants of the male parent selection.

Plants of the new *Echinacea* can be compared to plants of *Echinacea purpurea* 'Butterfly Kisses', disclosed in U.S. Plant Pat. No. 24,458. In side-by-side comparisons conducted in Zuidwolde, The Netherlands, plants of the new *Echinacea* differed primarily from plants of 'Butterfly Kisses' in the following characteristics:

1. Plants of the new *Echinacea* were taller than plants of 'Butterfly Kisses'.
2. Plants of the new *Echinacea* have lighter red purple-colored florets than plants of 'Butterfly Kisses'.

BRIEF DESCRIPTION OF THE PHOTOGRAPHS

The accompanying photographs illustrate the overall appearance of the new *Echinacea* plant showing the colors as true as it is reasonably possible to obtain in colored reproductions of this type. Colors in the photographs may differ slightly from the color values cited in the detailed botanical description which accurately describe the colors of the new *Echinacea* plant.

The photograph on the first sheet is a side perspective view of a typical flowering plant of 'Minbel252' grown in ground beds in an outdoor nursery and placed in a 21 cm container for the photograph.

The photographs on the second sheet are close-up views of a typical inflorescence (upper photograph) and the upper surface of a typical leaf (lower photograph) of 'Minbel252'.

DETAILED BOTANICAL DESCRIPTION

The aforementioned photographs and following observations and measurements describe plants grown during the summer in ground beds in an outdoor nursery in Zuidwolde, The Netherlands and under cultural practices typically used in commercial *Echinacea* production. During the production of the plants, day temperatures ranged from 18° C. to 32° C. and night temperatures ranged from 8° C. to 20° C. Plants were eight months old when the photographs and description were taken. In the following description, color references are made to The Royal Horticultural Society Colour Chart, 2007 Edition, except where general terms of ordinary dictionary significance are used.

Botanical classification: *Echinacea hybrida* 'Minbel252'.

Parentage:

*Female parent.*—*Echinacea hybrida* 'Southern Belle', disclosed in U.S. Plant Pat. No. 23,493.

*Male parent.*—Proprietary selection of *Echinacea hybrida* identified as code number 808-25, not patented.

Propagation:

*Type.*—By in vitro meristem culture.

*Time to initiate roots, summer.*—About one week at temperatures about 25° C.

*Time to produce a rooted young plant, summer.*—About five weeks at temperatures about 21° C.

*Root description.*—Fine, fibrous; typically pale cream in color, actual color of the roots is dependent on substrate composition, water quality, fertilizer type and formulation, substrate temperature and physiological age of roots.

*Rooting habit.*—Freely branching; medium density.

Plant description:

*Plant form and growth habit.*—Herbaceous perennial; upright and relatively compact plant habit, broad inverted triangle; freely branching habit with about 19 lateral branches developing per plant; vigorous growth habit.

*Plant height.*—About 60.5 cm.

*Plant diameter or spread.*—About 81.5 cm.

*Lateral branches.*—Length: About 40 cm. Diameter: About 5 mm. Internode length: About 6.3 cm. Aspect: Erect to about 30° from vertical. Strength: Strong. Texture: Moderately pubescent; strigose; rough. Color: Close to 146C to 146D tinged with close to 183A.

Leaf description:

*Basal leaves.*—Arrangement: Alternate, simple. Length: About 12.1 cm. Width: About 3 cm. Shape: Narrowly ovate to lanceolate. Apex: Acute. Base: Attenuate. Margin: Entire to very shallowly dentate; slightly undulate. Texture and luster, upper and lower surfaces: Moderately pubescent, strigose; rough; slightly glossy. Venation pattern: Pinnate. Color: Developing leaves, upper surface: Slightly darker than 143A. Developing leaves, lower surface: Close to 143A. Fully expanded leaves, upper surface: Close to NN137D; venation, close to 138B to 138C. Fully expanded leaves, lower surface: Close to 137B; venation, close to 138B to 138C. Petioles, basal leaves: Length: About 3.5 cm. Diameter: About 2.5 mm. Height: About 2.5 mm. Strength: Strong, flexible. Texture and luster, upper and lower surfaces: Mostly glabrous; margins, moderately pubescent, strigose; slightly glossy. Color, upper surface: Close to 145A; margins, close to NN137A. Color, lower surface: Close to 145A; margins, close to 137A.

*Cauline leaves.*—Arrangement: Alternate, simple. Length: About 8.3 cm. Width: About 1.3 cm. Shape: Narrowly ovate to lanceolate. Apex: Acute. Base: Attenuate. Margin: Entire to very shallowly dentate; slightly undulate. Texture and luster, upper and lower surfaces: Moderately pubescent, strigose; rough; slightly glossy. Venation pattern: Pinnate. Color: Developing leaves, upper surface: Slightly darker than 143A. Developing leaves, lower surface: Close to 143A. Fully expanded leaves, upper surface: Close to NN137D; venation, close to 138B to 138C. Fully expanded leaves, lower surface: Close to 137B; venation, close to 138B to 138C. Petioles, cauline leaves: Length: About 3 mm. Diameter: About 2 mm. Height: About 2 mm. Strength: Strong, flexible. Texture and luster, upper and lower surfaces: Mostly glabrous; margins, moderately pubescent, strigose; slightly glossy. Color, upper surface: Close to 145A; margins, close to NN137A. Color, lower surface: Close to 145A; margins, close to 137A.

Inflorescence description:

*Appearance.*—Large anemone-centered inflorescences with ray and disc florets arranged on a capitulum;

inflorescences positioned upright above the foliar plane on mostly upright and strong peduncles.

*Flowering habit*.—Freely flowering habit with about 130 inflorescences developing per plant during the flowering season.

*Fragrance*.—None detected.

*Time to flower*.—In the garden, plants flower continuously from early July to late September in The Netherlands.

*Inflorescence longevity*.—Inflorescences maintain good substance for about three weeks on the plant; inflorescences persistent.

*Inflorescence buds*.—Height: About 2.2 cm. Diameter: About 2.2 cm. Shape: Flattened globular. Color: Involucral bracts, darker than 146A; ray florets, close to 181B to 181C.

*Inflorescence size*.—Diameter: About 9.6 cm. Depth (height): About 4 cm. Disc diameter: About 6.8 cm. Receptacle height: About 1.4 cm. Receptacle diameter: About 8 mm. Receptacle color: Close to N155A.

*Ray florets*.—Quantity and arrangement: About 13 arranged in a single whorl at the base of the receptacle. Length: About 4.4 cm. Width: About 1 cm. Shape: Oblanceolate. Apex: Emarginate to praemorse. Base: Cuneate. Margin: Entire. Texture, upper surface: Glabrous; slightly velvety; longitudinally ridged. Texture, lower surface: Glabrous; longitudinally ridged. Luster, upper surface: Dull. Luster, lower surface: Slightly glossy. Aspect: Horizontal to drooping, about 5° from horizontal. Color: When opening, upper surface: Close to between 63B and 68A. When opening, lower surface: Close to 63A to 63B. Fully opened, upper surface: Close to 61A; color becoming closer to 182D with development. Fully opened, lower surface: Close to 67B and 68A; color becoming closer to 182C with development.

*Disc florets*.—Quantity and arrangement: About 240 per inflorescence, spirally at the center. Length: About 3 cm. Diameter: About 6 mm. Shape: Obovate to oblanceolate. Apex: Praemorse to cleft. Base: Cuneate, fused. Margin: Entire. Texture, upper surface: Smooth, glabrous; slightly velvety. Texture, lower surface: Smooth, glabrous. Luster, upper surface: Matte. Luster, lower surface: Slightly glossy. Color: When opening, upper surface: Close to 62A. When opening, lower surface: Close to 58D. Fully opened, upper surface: Close to 63B; color does not change with development. Fully opened, lower surface: Close to 63A to 63B; color does not change with development.

*Receptacle spines*.—Quantity: One per disc floret. Shape: Acicular. Apex: Acute. Base: Attenuate. Texture: Smooth, glabrous. Luster: Glossy. Color: Apex: Close to 53B. Mid-section: Close to 144B. Base: Close to 157D.

*Involucral bracts*.—Quantity per inflorescence: About 48 arranged in about three whorls. Length: About 7 mm. Width: About 3 mm. Shape: Ovate. Apex: Acute. Base: Cuneate. Margin: Entire. Texture, upper surface: Smooth, glabrous. Texture, lower surface: Moderately pubescent. Luster, upper and lower surfaces: Matte. Color, upper surface: Close to N137A. Color, lower surface: Close to 137A.

*Peduncles*.—Length: About 18.1 cm. Diameter: About 4 mm. Strength: Strong. Aspect: Upright to about 30° from vertical. Texture: Moderately pubescent; strigose. Color: Close to 146B to 146C.

*Reproductive organs*.—Androecium: None observed on ray or disc florets. Gynoecium (present only on disc florets): Quantity per floret: One. Pistil length: About 6 mm. Stigma shape: Decurrent, unequal. Stigma color: Close to 180C to 180D. Style length: About 5 mm. Style color: Close to 180C. Ovary color: Close to 157D. Seeds and fruits: Seed and fruit development have not been observed on plants of the new *Echinacea*.

Disease & pest resistance: Plants of the new *Echinacea* have not been shown to be resistant to pathogens and pests common to *Echinacea* plants.

Garden performance: Plants of the new *Echinacea* have exhibited good garden performance and to tolerate rain and wind. Plants of the new *Echinacea* have been observed to tolerate high temperatures of about 35° C. and to be hardy to USDA Hardiness Zones 3 to 4.

It is claimed:

1. A new and distinct *Echinacea* plant named 'Minbel252' as illustrated and described.

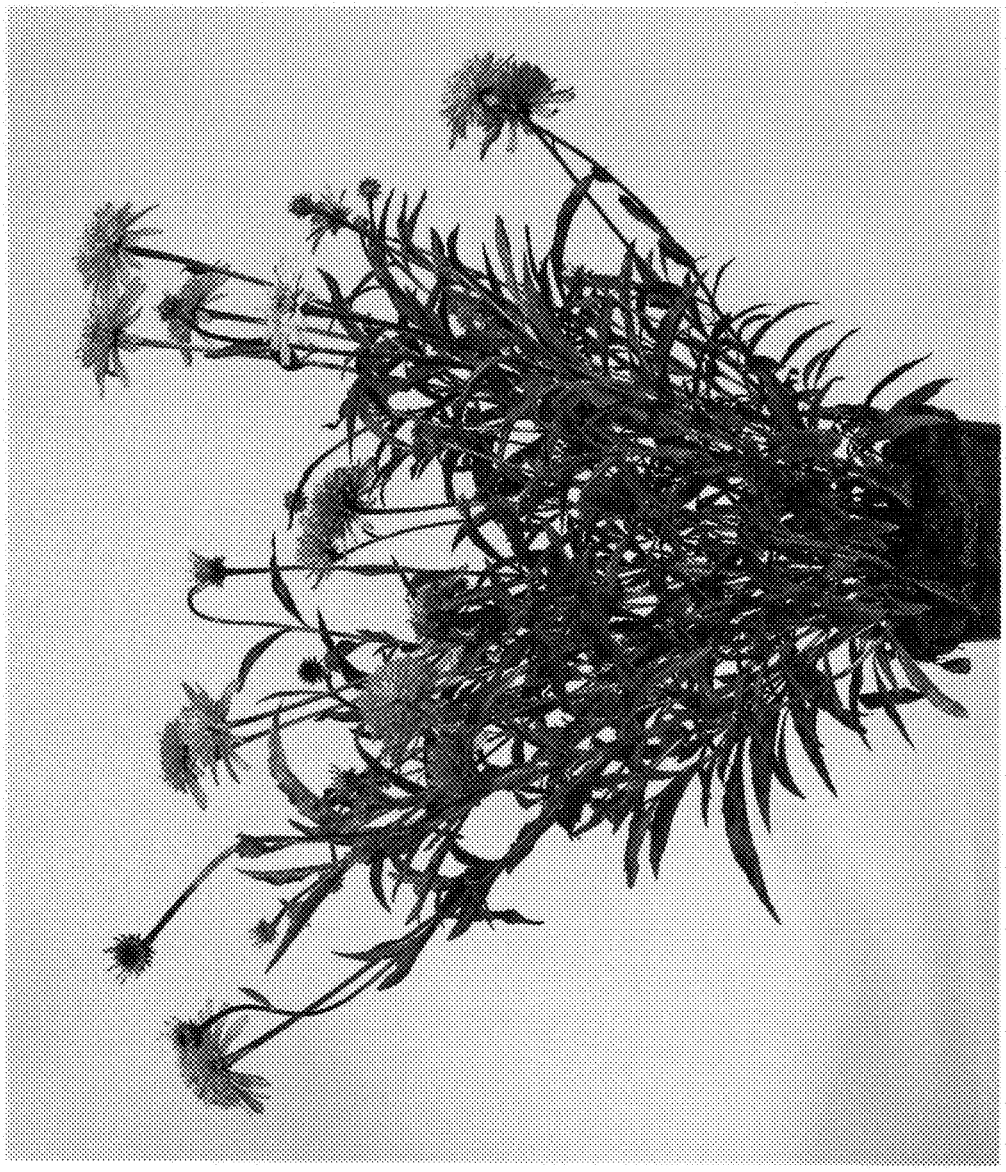

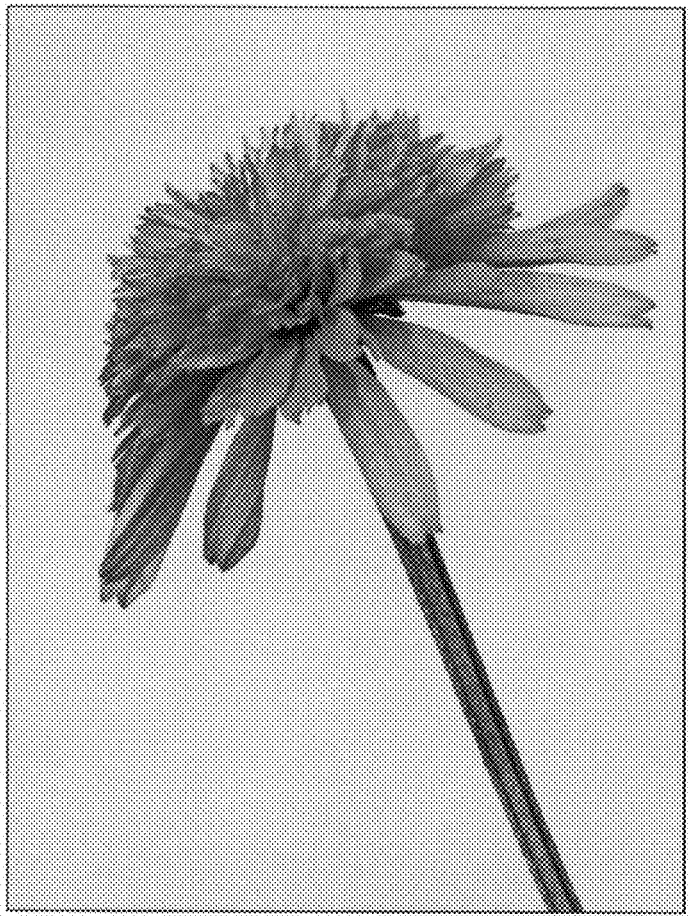
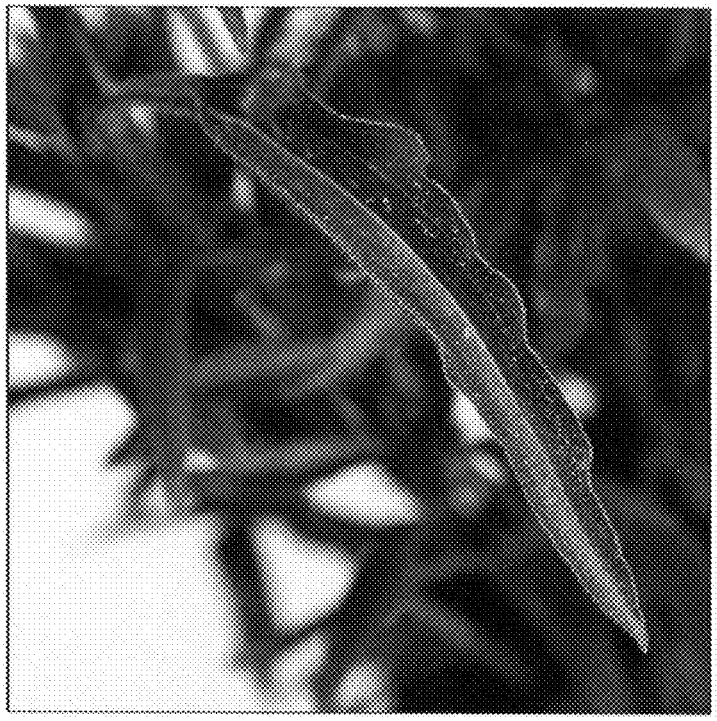

* * * * *